United States Patent
Graham (10) Patent No.: US 8,491,541 B2
(45) Date of Patent: Jul. 23, 2013

(54) BALL-VALVE ACTUATION MECHANISM

(75) Inventor: Joseph Graham, Canton, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 12/241,442

(22) Filed: Sep. 30, 2008

(65) Prior Publication Data
US 2010/0082016 A1    Apr. 1, 2010

(51) Int. Cl.
*A61M 5/00*    (2006.01)
(52) U.S. Cl.
USPC ....... 604/248; 604/246; 604/249; 251/315.06
(58) Field of Classification Search
USPC .................. 604/32, 248, 249; 251/315.06
See application file for complete search history.

(56) References Cited

U.S. PATENT DOCUMENTS

| | | |
|---|---|---|
| 3,191,600 A | 6/1965 | Everett |
| 3,411,534 A | 11/1968 | Rose |
| 3,434,691 A | 3/1969 | Hamilton |
| 3,608,862 A * | 9/1971 | Paxton ........................ 251/229 |
| 4,079,737 A | 3/1978 | Miller |
| 4,512,372 A | 4/1985 | Lew et al. |
| 4,576,199 A | 3/1986 | Svensson |
| 4,595,005 A | 6/1986 | Jinotti |
| 4,648,868 A | 3/1987 | Hardwick et al. |
| 4,789,000 A | 12/1988 | Alanian |
| 5,053,003 A | 10/1991 | Dadson et al. |
| 5,084,031 A | 1/1992 | Todd et al. |
| 5,197,951 A | 3/1993 | Mahurkar |
| 5,269,768 A | 12/1993 | Cheung |
| 5,324,274 A | 6/1994 | Martin |
| 5,329,921 A | 7/1994 | Socaris et al. |
| 5,399,172 A | 3/1995 | Martin et al. |
| 5,472,432 A | 12/1995 | Martin |
| 6,162,201 A | 12/2000 | Cohen |
| 6,280,423 B1 | 8/2001 | Davey et al. |

(Continued)

FOREIGN PATENT DOCUMENTS

| | | |
|---|---|---|
| EP | 1 955 728 | 8/2008 |
| EP | 2 168 611 | 11/2011 |

(Continued)

OTHER PUBLICATIONS

Slide. 2010. In Merriam-Webster Online Dictionary. Retrieved Oct. 6, 2010, from http://www.merriam-webster.com/dictionary/slide.*

(Continued)

*Primary Examiner* — Emily Schmidt
(74) *Attorney, Agent, or Firm* — John Paul Mello, Esq.

(57) ABSTRACT

A valve assembly for use with a catheter assembly is provided. The valve assembly includes a valve housing defining a longitudinal axis and adapted for fluid engagement with a catheter assembly. The valve housing has an internal passageway for flow of fluids relative to the catheter assembly. A valve member is at least partially disposed within the valve housing and defines a valve passage. The valve member is adapted for movement within the valve housing between an open position wherein the valve passage is in general alignment with the internal passageway of the valve housing to permit flow of fluids through the valve housing, and a closed position to substantially occlude the internal passageway of the valve housing. An actuation mechanism is selectively movable in a general longitudinal direction to cause corresponding movement of the valve member between the open position and the closed position.

11 Claims, 10 Drawing Sheets

U.S. PATENT DOCUMENTS

| | | |
|---|---|---|
| 6,332,892 B1 | 12/2001 | Desmond, III et al. |
| 6,595,966 B2 | 7/2003 | Davey et al. |
| 6,620,202 B2 | 9/2003 | Bottcher et al. |
| 6,656,146 B1 | 12/2003 | Clayman et al. |
| 6,719,804 B2 | 4/2004 | St. Pierre |
| 6,849,069 B1 | 2/2005 | Clayman et al. |
| 6,918,893 B2 | 7/2005 | Houde et al. |
| 6,945,950 B2 | 9/2005 | Clayman et al. |
| 6,991,614 B2 | 1/2006 | McWeeney et al. |
| 7,011,645 B2 | 3/2006 | McGuckin et al. |
| 7,037,345 B2 | 5/2006 | Bottcher et al. |
| 7,041,080 B2 | 5/2006 | Dion |
| 7,172,572 B2 | 2/2007 | Diamond et al. |
| 7,211,074 B2 | 5/2007 | Sansoucy |
| 7,291,180 B2 | 11/2007 | St. Pierre |
| 7,393,339 B2 | 7/2008 | Zawacki et al. |
| 7,410,602 B2 | 8/2008 | Davey et al. |
| 2008/0319401 A1* | 12/2008 | Funamura et al. ............ 604/248 |

FOREIGN PATENT DOCUMENTS

| | | |
|---|---|---|
| WO | 91/03217 | 3/1991 |
| WO | WO 91/03217 | 3/1991 |
| WO | 91/06331 | 5/1991 |
| WO | WO 91/06331 | 5/1991 |

OTHER PUBLICATIONS

European Search Report dated Feb. 17, 2010.
European Search Report for EP09170847 date of completion is Feb. 1, 2010 (3 pages).
Chinese Office Action (with translation) dated Oct. 10, 2012 in copending Chinese Application No. 200910204452.0.
Chinese Office Action dated Apr. 19, 2013 in copending Chinese Application No. 200910204452.

* cited by examiner

FIG. 8

US 8,491,541 B2

BALL-VALVE ACTUATION MECHANISM

BACKGROUND

1. Technical Field

The present disclosure relates to valve assemblies for catheter systems. More particularly, the present disclosure relates to valve assemblies including linear actuation mechanisms for rotating a ball-valve to open and close a fluid passageway within the assemblies.

2. Background of Related Art

Access catheters may be single lumen, dual lumen or multi-lumen and may be used for a variety of procedures, including dialysis and urine collection. The main body of the catheter is designed for operable engagement with a patient and the proximal or outer end includes extensions, one for each lumen. It is common practice to make these extensions from flexible tubing so that the tubing may be manipulated outside the body and held in any convenient position using surgical dressings. The tubing generally carries a luer lock connector at its free end for attachment to fluid lines and for subsequent closing and sealing of the lumens when the catheter is not in use. Because these connectors have a tendency of failing, it is also common practice to place a clamp on each of the extensions to deform the tubing and to act as a second closure mechanism.

Flexible tubes and clamps are unsatisfactory for use in access catheters for a number of reasons. The most serious problem is that, because the clamps close the tubing through a pinching action, if the clamp is in place for a significant length of time, the tubing may not recover when the clamp is released. The resulting crease in the tubing causes flow problems, and in extreme cases, the catheter has to be removed because the tube is no longer patent. This problem is most prevalent on catheters that have thermoplastic tubular extensions made from polyvinylcholoride (PVC) or polyurethane (PU).

It has also been found that unless the clamps used to pinch closed the tubing are aligned accurately before engaging the tubing, the clamps may disengage by a minor impact. Furthermore, conventional clamps tend to have sharp edges which are required to crease the tubing. These sharp edges may result in cutting and/or shearing of the tubing, particularly when silicone rubber tubing is used.

Accordingly, a continuing need exists for a valve assembly for use in an access catheter that includes at least one actuation mechanism for regulating the flow through the catheter without detriment to the catheter or tubing.

SUMMARY

A valve assembly for use with a catheter assembly is provided. The valve assembly includes a valve housing adapted for fluid engagement with a catheter assembly, the valve housing defining a longitudinal axis and having an internal passageway for flow of fluids relative to the catheter assembly, a valve member at least partially disposed within the valve housing and defining a valve passage, the valve member adapted for movement within the valve housing between an open position wherein the valve passage is in general alignment with the internal passageway of the valve housing to permit flow of fluids through the valve housing, and a closed position to substantially occlude the internal passageway of the valve housing, and an actuation mechanism mounted to the valve housing and operatively connected to the valve member, the actuation mechanism selectively movable in a general longitudinal direction to cause corresponding movement of the valve member between the open position and the closed position.

The valve member may be adapted for rotational movement within the valve housing to move between the open position and the closed position thereof. The valve passage of the valve member may be generally misaligned relative to the internal passageway of the valve housing when in the closed position of the valve member. The valve member may define a generally spherical shape. The actuation mechanism may be movable relative to the valve housing between a first position corresponding to the open position of the valve member and a second position corresponding to the closed position of the valve member. The actuation mechanism may be adapted to be releasably locked relative to the valve housing when in at least one of the first and second positions thereof.

The valve housing may further include a cantilever member engageable with the actuation mechanism to selectively releasably secure the actuation mechanism in the one of the first and second positions thereof. A release member may be mounted with respect to the actuation mechanism and selectively movable to cause corresponding movement of cantilever member and release thereof from operative engagement with a lock member of the actuation mechanism, to hereby permit movement of the actuation mechanism. The release member may normally be biased to a position corresponding to a secured condition of the cantilever member relative to the actuation mechanism. The lock member may engage the cantilever member, the cantilever member adapted to pivot from the secured condition to an unsecured condition relative to the actuation mechanism upon movement of the release member to thereby permit movement of the actuation mechanism.

The actuation mechanism may be adapted to be releasably locked relative to the valve housing when in each of the first and second positions thereof. The valve assembly may further include first and second cantilever members, the first cantilever member may be adapted to releasably secure the actuation mechanism in the first position thereof, the second cantilever member adapted to releasably secure the actuation mechanism in the second position thereof. Each of the first and second cantilever members may be adapted to pivot to the unsecured condition relative to the actuation mechanism upon movement of the release member. The release member may normally be biased to an unactuated position thereof corresponding to the secured condition of the cantilever member. The valve housing may include a coupling adapted for connection to the catheter assembly.

Another embodiment of a valve assembly for use with a catheter assembly is also provided. The valve assembly includes a valve housing adapted for fluid engagement with a catheter assembly, the valve housing defining a longitudinal axis and having an internal passageway for flow of fluids relative to the catheter assembly, a valve member at least partially disposed within the valve housing and defining a valve passage, the valve member adapted for movement within the valve housing between an open position wherein the valve passage is in general alignment with the internal passageway of the valve housing to permit flow of fluids through the valve housing, and a closed position to substantially occlude the internal passageway of the valve housing, and an actuation mechanism mounted to the valve housing and operatively connected to the valve member, the actuation mechanism selectively movable between a first position corresponding to the open position of the valve member and a second position corresponding to the closed position of the valve member, the actuation mechanism being adapted to be releasably locked relative to the valve housing when in at least one of the first and second positions thereof.

The actuation mechanism may be adapted to be releasably locked in each of the first and second positions thereof. The valve housing may include first and second cantilever members, the first cantilever member adapted to releasably secure the actuation mechanism in the first position thereof, the second cantilever member adapted to releasably secure the actuation mechanism in the second position thereof.

A release member may be mounted with respect to the actuation mechanism and selectively movable to cause corresponding movement of one of the first and second cantilever members to cause release of the one of the first and second cantilever members from operative engagement with the actuation mechanism, to thereby permit movement of the actuation mechanism. The first and second cantilever members adapted to pivot from a secured condition to an unsecured condition relative to the actuation mechanism upon movement of the release member to thereby permit movement of the actuation mechanism, each cantilever member being normally biased toward the secured condition thereof.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
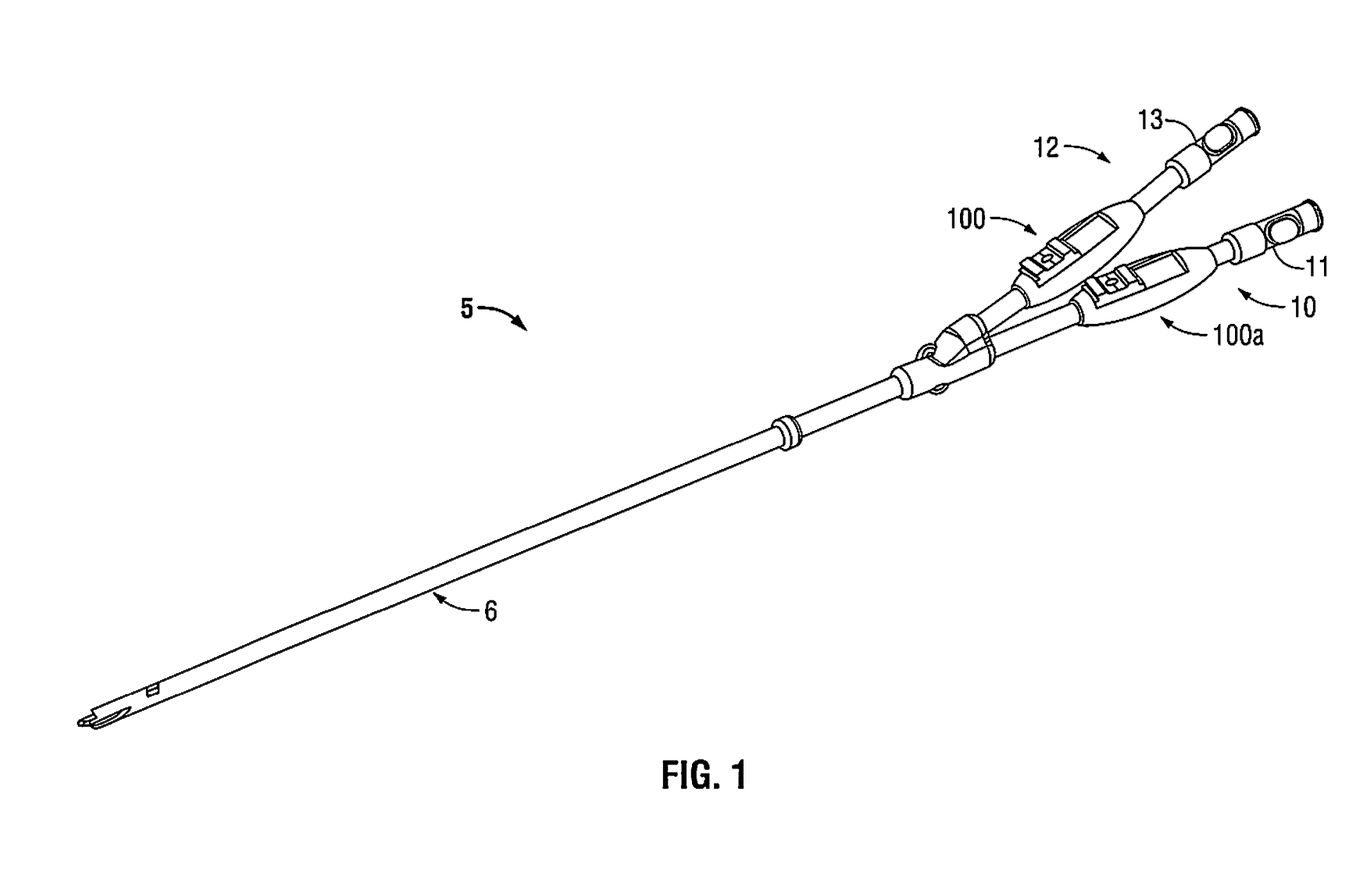
FIG. 1 is a perspective view of a catheter assembly including an embodiment of valve assemblies according to the present disclosure.

Referring initially to FIG. 1, a catheter assembly including valve assemblies according to an embodiment of the present disclosure is shown generally as catheter assembly 5. Briefly, catheter assembly 5 includes a dual lumen shaft 6 on a first end and a pair of tubular extensions 10, 12 on an opposite end. Tubular extensions 10, 12 are fluidly coupled to shaft 6 and include connectors 11, 13, respectively, and valve assemblies 100, 100a. Although the embodiments of the present disclosure will be described as relates to catheter assembly 5, the valve assemblies of the present disclosure should not be read as limited to use with catheter assembly 5. It is envisioned that the embodiments of the present disclosure may be modified for use with various fluid systems, including but not limited to, dialysis, urine collection, enteral feeding and breathing assistance.

Figure 2A:
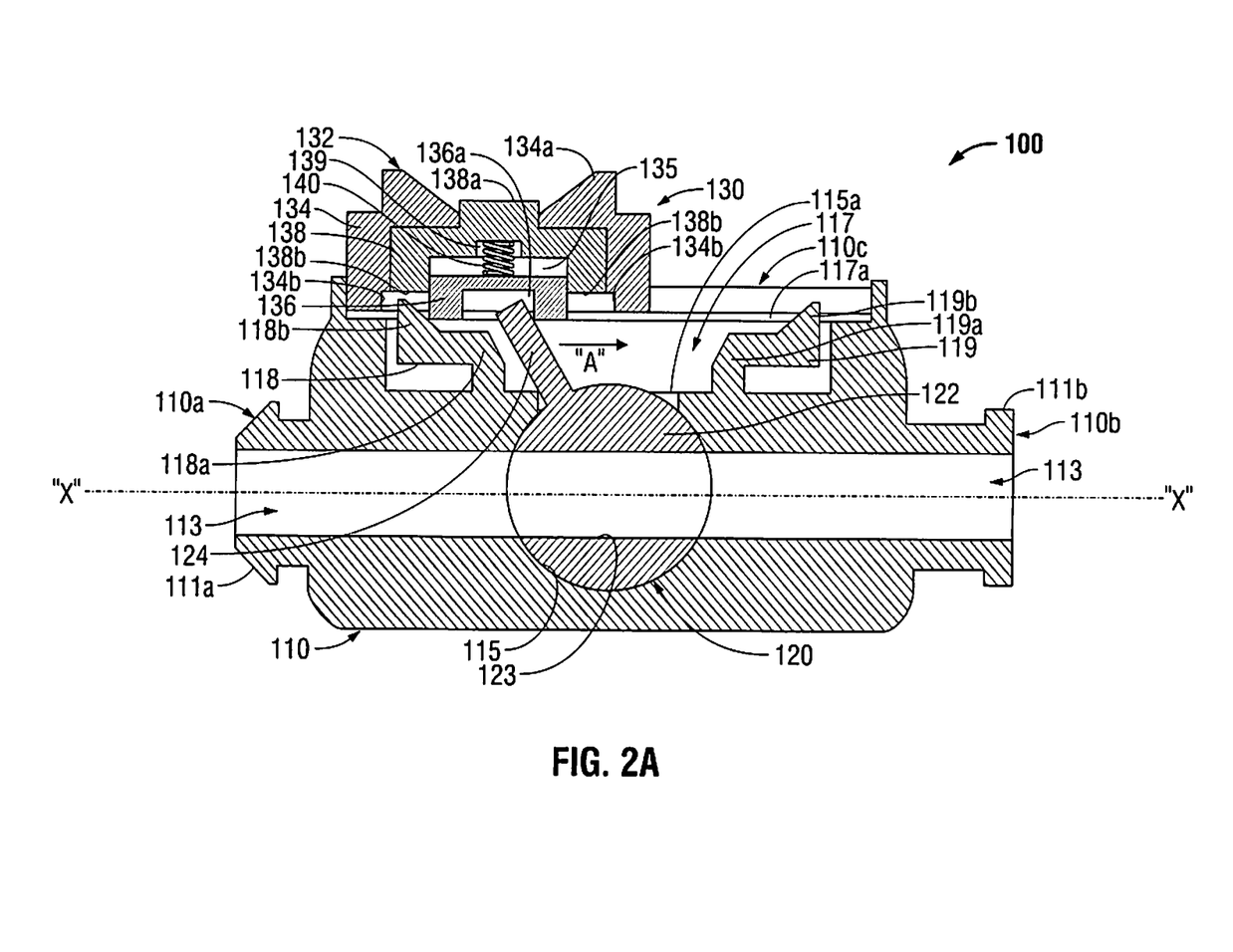
FIG. 2A is a partial cross-sectional side view of the valve assembly of the catheter assembly of FIG. 1, in a first or open condition.
Figure 2B:
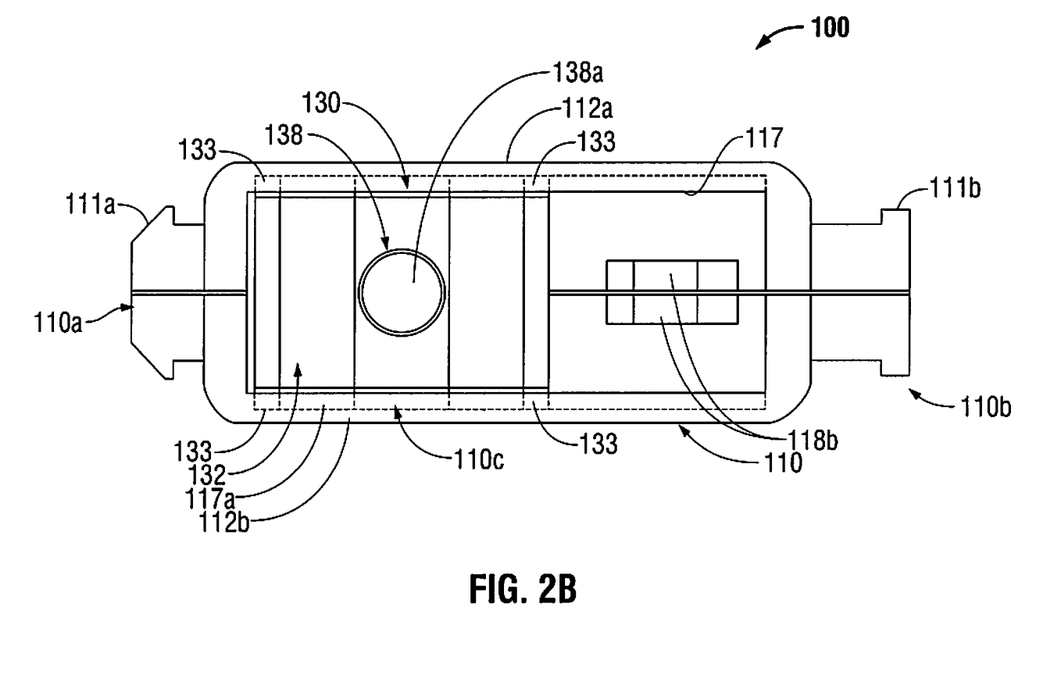
FIG. 2B is a top view of the valve assembly of FIG. 2A.

Still referring to FIG. 1, valve assemblies 100, 100a are substantially identical to each other and will be described with reference to valve assembly 100. With reference now to FIGS. 2A and 2B, valve assembly 100 includes a valve housing 110, a valve member 120 rotatably received within valve housing 110, and an actuation mechanism 130 slidably mounted to valve housing 110 and operably engaged with valve member 120.

Figure 5:
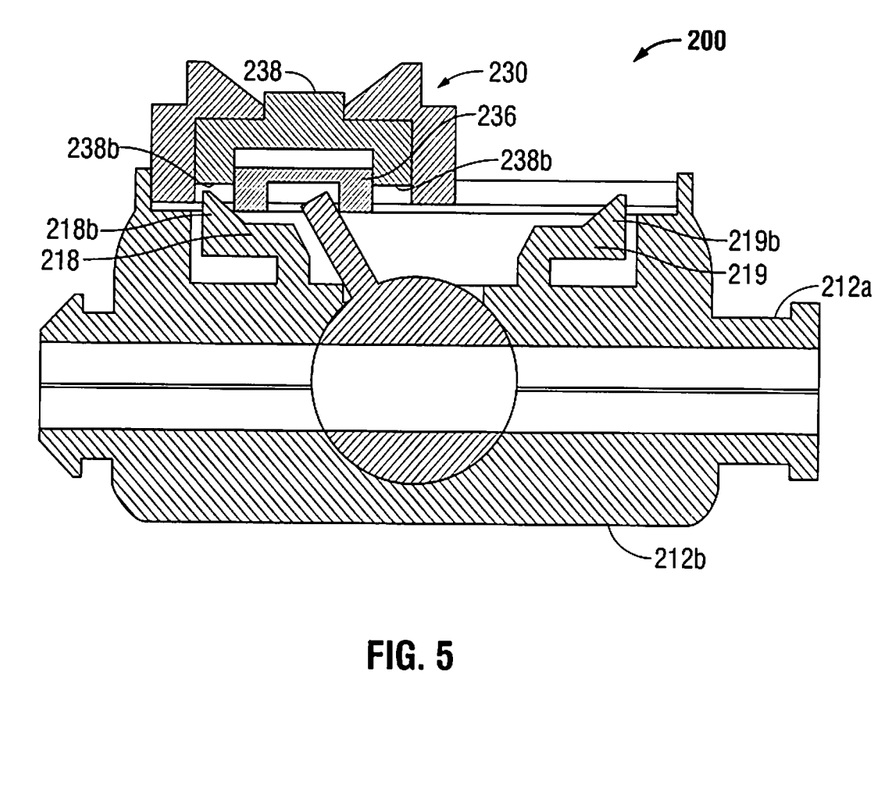
FIG. 5 is cross-sectional side view of an alternative embodiment of a valve assembly according to the present disclosure, in a first or open condition.
Figure 6:
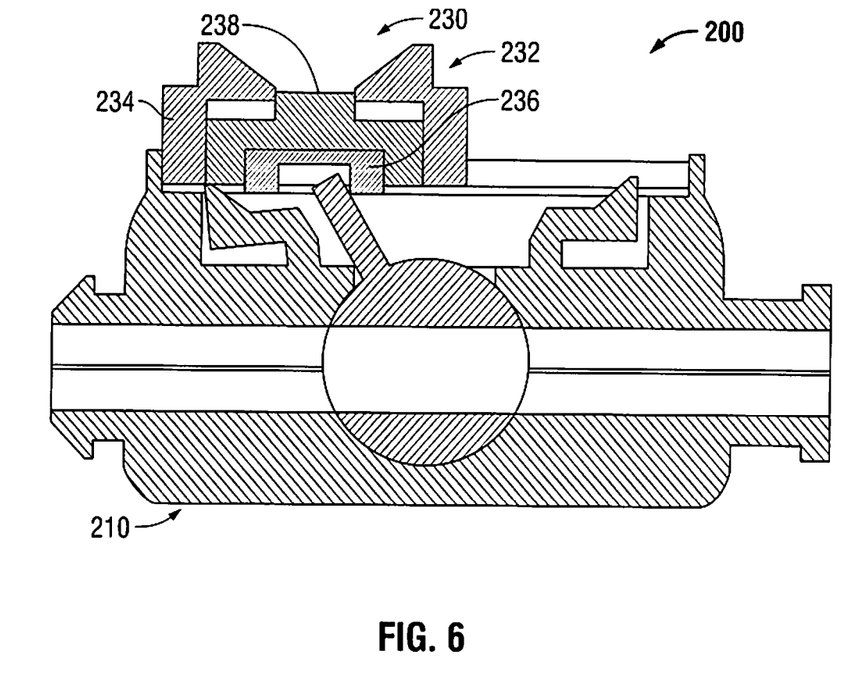
FIG. 6 is a cross-sectional side view of the valve assembly of FIG. 5, with a release member in a depressed condition.

With reference still to FIGS. 2A and 2B, valve housing 110 includes first and second housing halves 112a, 112b. Housing halves 112a, 112b may be formed as shown in FIG. 2B, as mirror image first and second sides, 112a, 112b, or housing 110 may be divided into top and bottom sections 212a, 212b (FIG. 5). Housing halves 112a, 112b are affixed to one another using any conventional method, including, adhesive, glue, chemical bonding, ultrasonic welding, snap-fit connection, and mechanical fasteners. Housing 110 defines a longitudinal axis "X" and includes a proximal end 110a, a distal end 110b and an internal passageway 113 therebetween. In one embodiment, proximal and distal ends 110a, 110b include connection fittings 111a, 111b. In an alternative embodiment, proximal and/or distal ends 110a, 110b may be integrally formed within catheter assembly 5 (FIG. 1).

Figure 4A:
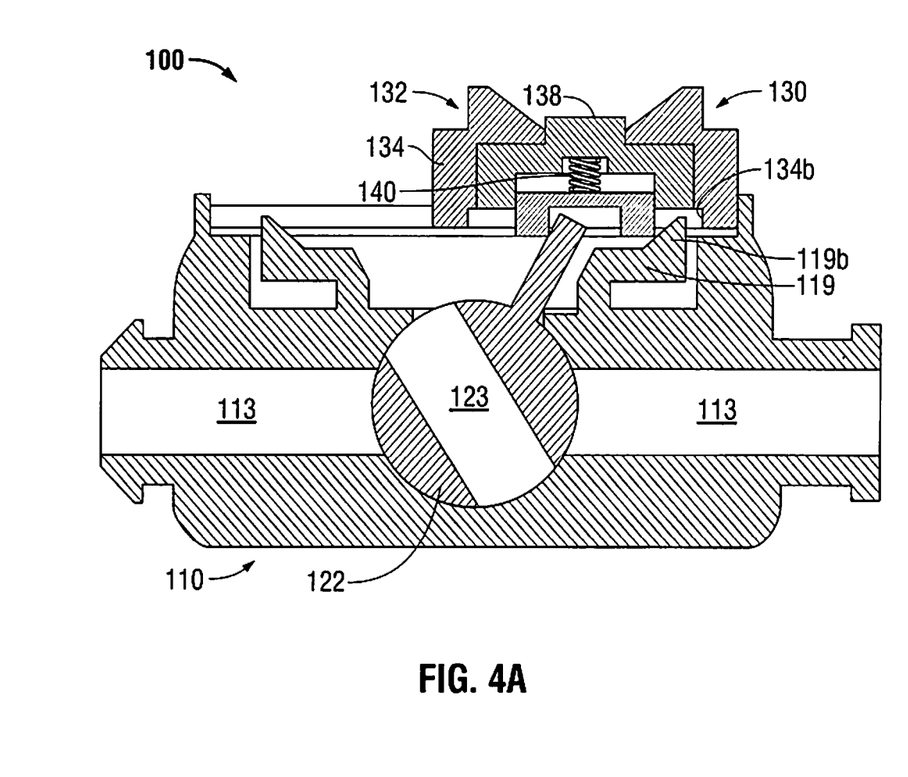
FIG. 4A is a partial cross-sectional side view of the valve assembly of FIGS. 2A-3, in a second or closed condition.

Still referring to FIGS. 2A and 2B, a spherical cut-out portion 115 is formed along internal passageway 113 of valve housing 110. Cut-out portion 115 is sized and dimensioned to receive valve member 120. As will be discussed in further detail below, valve member 120 defines a substantially spherical member in the form of a ball-valve 122. Cut-out portion 115 includes an open top end 115a configured for receipt of a stem 124 extending from ball-valve 122. As will also be discussed in further detail below, the length of open top end 115a of cut-out portion 115 is dependent upon the angle though which ball-valve 122 must move to rotate from an open position (FIG. 2A) to a closed position (FIG. 4A). The less the degree of rotation, the smaller open top end 115a may be. The converse is also true, the larger the degree of rotation needed to open or close ball-valve 122, the larger open top 115a must be.

A top surface 110c of valve housing 110 is configured to slidingly receive actuation mechanism 130. Top surface 110c defines a recessed portion 117. Recessed portion 117 includes opposed rails or grooves 117a extending along a length thereof to operably engage lock member 132 of actuation mechanism 130. Grooves 117a are configured to receive tabs 133 formed on lock member 132. Grooves 117a extend the length of recessed portion 117 and are configured such that lock member 132 may traverse the length of recessed portion 117 from a first locked position (FIG. 2A) to a second locked position (FIG. 4A). Recessed portion 117 further includes opposed cantilever members 118, 119. Cantilever members 118, 119 may be formed on one or both of housing halves 112a, 112b and may extend the width of recessed portion 117. Cantilever members 118, 119 include inner first ends 118a, 119a, respectively, securely affixed to housing 110 and outer second ends 118b, 119b, respectively, extending along and spaced from housing 110. Outer second ends 118b, 119b flex relative to housing 110. In this manner, outer second ends 118b, 119b are configured to selectively engage engagement surfaces 134b formed on first section 134 of lock member 132.

Turning briefly to FIG. 2A, as noted above, valve member 120 includes a ball-valve 122 having a stem 124 extending therefrom. Ball-valve 122 is sized and dimensioned to be received in cut-out 115 of valve housing 110. When ball-valve 122 is received in cut-out 115 stem 124 extends through open top end 115a to engage recess 136a formed in second section 136 of lock member 132. Ball-valve 122 defines a passage 123 configured to align with internal passageway 113 of valve housing 110 when valve assembly 100 is in the first or open position (FIG. 2A) to permit the flow of fluid (not shown) through valve assembly 100. Advancement of stem 124, in the direction of arrow "A" within top open end 115a of cut-out 115 causes rotation of ball-valve 122, and thus, misalignment of passage 123 and internal passageway 113. As discussed above, top open end 115a of cut-out 115 is of a length sufficient to permit advancement of stem 124 to cause rotation of ball-valve 122 from a first position (FIG. 2A) where passage 123 and internal passageway 113 are completely aligned, to a second position (FIG. 4A) where passage 123 and internal passageway 113 are completely misaligned.

The diameters of ball-valve 122 and passage 123 determine the linear distance stem 124 must travel to ensure complete misalignment of passage 123 and internal passageway 113. For example, if ball-valve 122 is ten millimeters (10 mm) in diameter and passage 123 measures five millimeters (5 mm) in diameter, stem 124 would be required to travel five point eight millimeters (5.8 mm) or through sixty degrees (60°) of rotation to rotate ball-valve 122 from the first position to the second position. Reducing the diameter of ball-valve 122 to about seven millimeters (~7 mm) while maintaining passage 123 at five millimeters (5 mm) would require a minimum linear travel distance of stem 124 of seven millimeters (7 mm) or through ninety degrees (90°) of rotation.

Figure 4B:
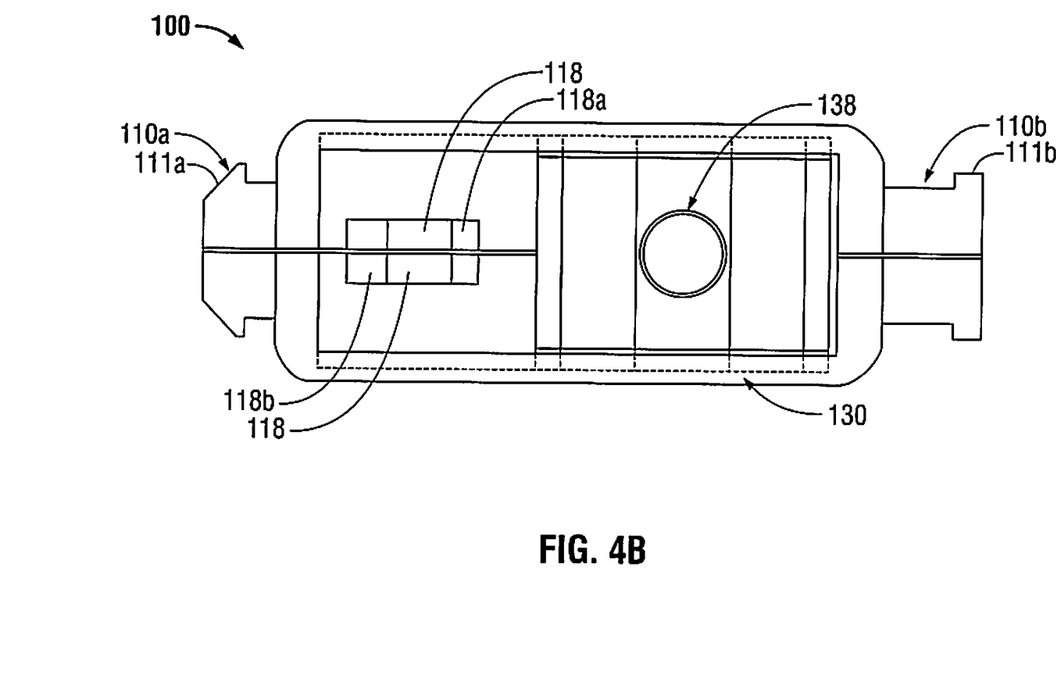
FIG. 4B is a top view of the valve assembly of FIG. 4A.

With reference back to FIGS. 2A and 2B, actuation mechanism 130 includes lock member 132, a release member 138, and a biasing member 140. Actuation mechanism 130 is configured to be selectively positioned relative to valve housing 110 from at least the first or open position (FIG. 2A) to at least the second or closed position (FIG. 4B). In one embodiment, actuation mechanism 130 is configured for engagement by the thumb of a clinician (not shown).

Lock member 132 includes first and second sections 134, 136 and defines an opening 135 therebetween for receipt of release member 138. First and second sections 134, 136 may be integrally formed, or instead may be securely affixed to one another using any conventional method, including, adhesive, glue, chemical bonding, ultrasonic welding, snap-fit connection, and mechanical fasteners. Preferably, first and second sections 134, 136 are not connected until release member 138 has been received therebetween. First section 134 defines a recessed portion 134a configured for operable engagement by a clinician. First section 134 further includes engagement surfaces 134b configured to engage outer second ends 118b, 119b of cantilever members 118, 119, respectively, when actuation mechanism 130 is in respective first (FIG. 2A) and second (FIG. 4A) positions. A plurality of opposed tabs 133 (FIG. 2B) extend outwardly from first section 134 and are configured to be received within grooves 117a formed in recessed portion 117 of valve housing 110. Tabs 133 permit actuation mechanism 130 to be slidably received within recess portion 117. In an alternative embodiment, tabs 133 may be formed along the entire length of first section 134. It is envisioned that second section 136 may also include tabs (not shown) configured to be slidably received in grooves 117a. In this manner, first and second sections 134, 136 would be maintained relative to each other without being integrally formed or with the use of conventional securing methods. Second section 136 includes a recess 136a configured to receive an end of stem 124 of ball-valve 122 extending through open top end 115a of cut-out 115 of valve housing 110.

Still referring to FIGS. 2A and 2B, release member 138 defines a substantially "C" shaped member including an engagement surface 138a configured to be pressed by a clinician and opposed contact surfaces 138b configured to engage outer second ends 118b, 119b of cantilever members 118, 119, respectively, formed on valve housing 110 when actuation mechanism 130 is in respective first and second positions. Release member 138 further includes a recess 139 configured to receive biasing member 140. Biasing member 140 extends between second section 136 and release member 138 to bias release member 138 away from second section 136. Biasing member 140 may be in the form of a spring, as shown, or may instead include a cantilever, pressure cylinder or other biasing element.

The operation of valve assembly 100 will now be described with reference to FIGS. 2A-4B. Referring initially to FIGS. 2A and 2B, valve assembly 100 is shown in a first or open condition. In this open condition, passage 123 of ball-valve 122 is completely aligned with internal passageway 113 of valve housing 110. When valve assembly 100 is in the open condition, engagement surface 134b of first section 134 engages outer second end 118b of cantilever 118, thereby maintaining actuation mechanism 130 locked in the first position.

Figure 3:
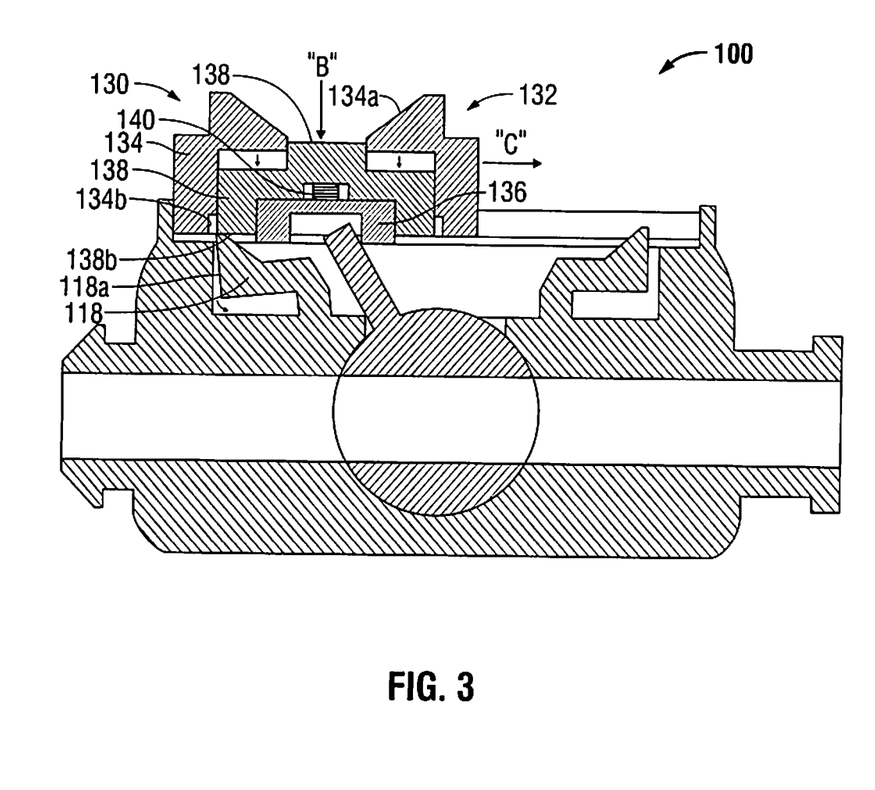
FIG. 3 is a partial cross-sectional side view of the valve assembly of FIGS. 2A and 2B, with a release member in a depressed condition.

Turning to FIG. 3, downward pressure by a clinician on engagement surface 138a of release member 138, in the direction of arrow "B", causes compression of biasing member 140 and approximation of release member 138 towards second section 136 of lock member 132. The downward movement of release member 138 causes engagement of contact surfaces 138b thereof with outer second end 118b of cantilever 118. Continued engagement of release member 138 with cantilever member 118 causes outer second end 118b of cantilever member 118 to flex away from and disengage engagement surface 134b of first section 134. Disengagement of engagement surface 134b by outer second end 118a of cantilever member 118 unlocks actuation mechanism 130 and permits linear movement of actuation mechanism. Advancement of actuation mechanism 130 in the direction of arrow "C" causes the rotation of ball-valve 122, thereby misaligning passage 123 of ball-valve 122 and internal passageway 113 of valve housing 110. When the clinician releases release member 138, biasing member 140 biases release member 138 back to an original position spaced from second section 136.

Turning to FIG. 4A and 4B continued advancement of actuation mechanism 130 causes linear movement of stem 124 of ball-valve 122 which results in continued rotation of ball-valve 122 until passage 123 of ball-valve 122 and internal passageway 113 of valve housing 110 are completely misaligned and internal passageway 113 is totally obstructed by ball-valve 122. In this closed or second position, opposed engagement surface 134b of first section 134 of lock member 132 engages outer second end 119b of cantilever 119. In this manner, actuation mechanism 130 is locked within recessed portion 117 of housing 110 in a second or closed position. Valve assembly 100 may be reopened by depressing release member 138 and advancing actuation mechanism 130 in an opposite direction.

Figure 7:
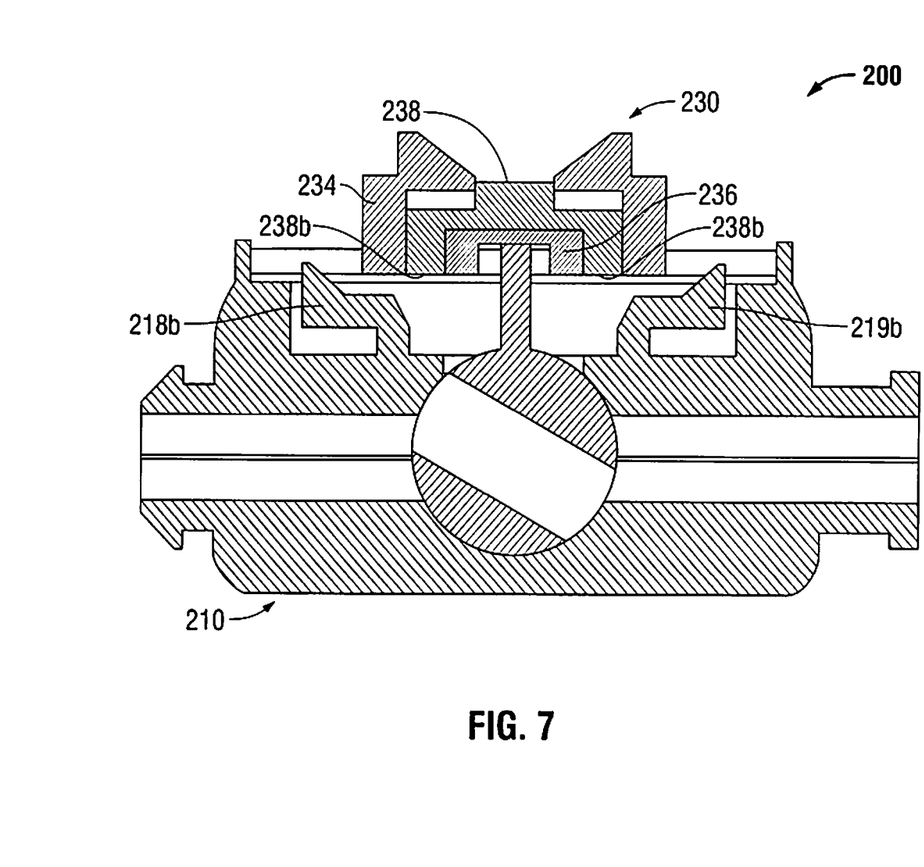
FIG. 7 is a cross-sectional side view of the valve assembly of FIGS. 5 and 6, in a intermediate condition.
Figure 8:
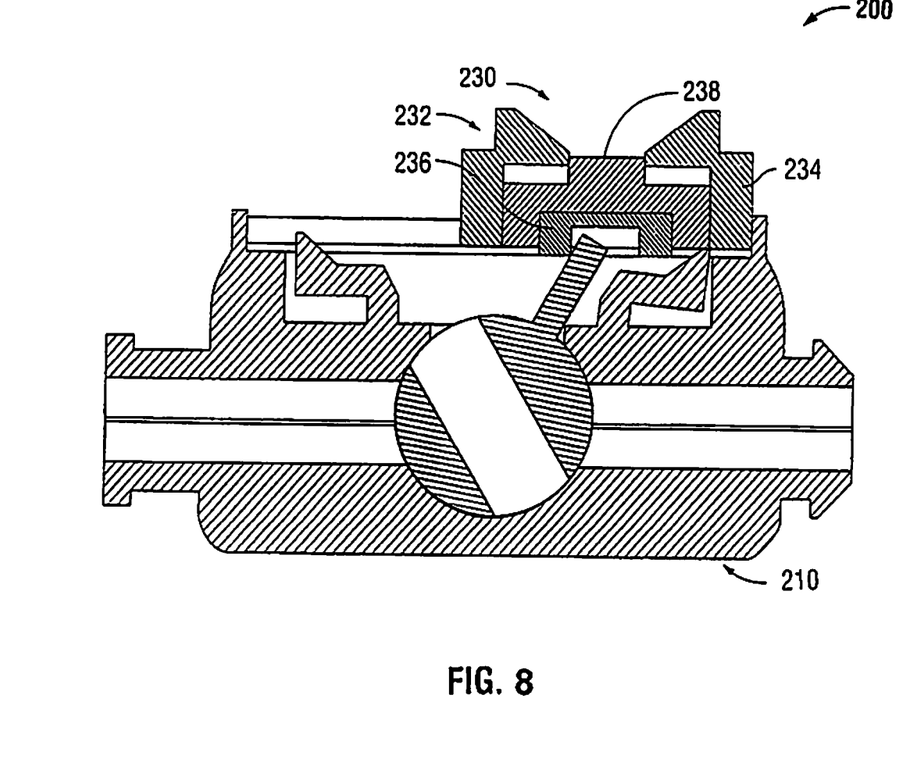
FIG. 8 is a cross-sectional side view of the valve assembly of FIGS. 5-7, in a second or closed condition.

With reference now to FIGS. 5-8, an alternate embodiment of a valve assembly according to the present disclosure is shown generally as valve assembly 200. Valve assembly 200 is substantially similar in form and function to valve assembly 100 and will only be described as relates to the difference therebetween. Similar reference numerals denote similar structure. Valve assembly 200 includes a housing 210 formed as housing top 212a and housing bottom 212b. Valve assembly 200 further includes an actuation mechanism 230 having a release member 238. Actuation mechanism 230 does not include a biasing member between release member 238 and a second section 236 of lock member 232. In this manner, release member 230 is loosely retained between a first section 234 and second section 236 of lock member 232 when contact surfaces 238b of release member 238 do not engage outer second ends 218b, 219b of cantilever members 218, 219 (FIG. 7). However, when actuation mechanism 230 is in either a first, open position (FIG. 5) or a second, closed position (FIG. 7) respective outer second ends 218b, 219b of cantilever members 218, 219, respectively, engage contact surfaces 238b of release member 238, biasing release member 238 away from second section 236. In this manner, release member 238 provides a clinician with a visual indication of whether actuation mechanism 230 is locked in the first or second positions or is instead in an intermediary position.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, it is envisioned that actuation mechanism 130 may be configured for automatic actuation by an electric motor or slide. In this manner, actuation mechanism 130 could be automatically actuated by a clinician without having to manually depress release member 138 and advance actuation mechanism 130. Additionally, actuation mechanism 130 may be configured for remote activation.

What is claimed is:

1. A valve assembly for use with a catheter assembly, which comprises:
a valve housing adapted for fluid engagement with a catheter assembly, the valve housing defining a longitudinal axis and having an internal passageway for flow of fluids relative to the catheter assembly;
a valve member at least partially disposed within the valve housing and defining a valve passage, the valve member adapted for rotational movement within the valve housing between an open position wherein the valve passage is in general alignment with the internal passageway of the valve housing to permit flow of fluids through the valve housing, and a closed position wherein the valve passage of the valve member is generally misaligned relative to the internal passageway of the valve housing to substantially occlude the internal passageway of the valve housing;
an actuation mechanism having a first end and a second end mounted to the valve housing and operatively connected to the valve member, the actuation mechanism being slidably supported on the valve housing in a general linear direction parallel to the longitudinal axis of the valve housing to cause corresponding movement of the valve member between the open position and the closed position;
wherein the actuation mechanism is movable relative to the valve housing between a first position corresponding to the open position of the valve member and a second position corresponding to the closed position of the valve member and the actuation mechanism is adapted to be releasably locked relative to the valve housing when in at least one of the first and second positions thereof;
wherein the valve housing includes a cantilever member, the cantilever member operatively engageable with the actuation mechanism to selectively releasably secure the actuation mechanism in the one of the first and second positions thereof; and
a release member mounted with respect to the actuation mechanism and selectively movable relative to the actuation mechanism to cause corresponding movement of the cantilever member and release thereof from operative engagement with the actuation mechanism, to thereby permit movement of the actuation mechanism.

2. The valve assembly according to claim 1 wherein the cantilever member is normally biased to a position corresponding to a secured condition of the cantilever member relative to the actuation mechanism.

3. The valve assembly according to claim 2 wherein the cantilever member is adapted to pivot from the secured condition to an unsecured condition relative to the actuation mechanism upon movement of the release member to thereby permit movement of the actuation mechanism.

4. The valve assembly according to claim 3 wherein the actuation mechanism is adapted to be releasably locked relative to the valve housing when in each of the first and second positions thereof.

5. The valve assembly according to claim 4 including first and second cantilever members, the first cantilever member adapted to releasably secure the actuation mechanism in the first position thereof, the second cantilever member adapted to releasably secure the actuation mechanism in the second position thereof.

6. The valve assembly according to claim 5 wherein each of the first and second cantilever members are adapted to pivot to the unsecured condition relative to the actuation mechanism upon movement of the release member.

7. The valve assembly according to claim 1 wherein the release member is normally biased to an unactuated position thereof corresponding to the secured condition of the cantilever member.

8. The valve assembly according to claim 1 wherein the valve housing includes a coupling adapted for connection to the catheter assembly.

9. A valve assembly for use with a catheter assembly, which comprises:
a valve housing adapted for fluid engagement with a catheter assembly, the valve housing defining a longitudinal axis and having an internal passageway for flow of fluids relative to the catheter assembly;
a valve member at least partially disposed within the valve housing and defining a valve passage, the valve member adapted for movement within the valve housing between an open position wherein the valve passage is in general alignment with the internal passageway of the valve housing to permit flow of fluids through the valve housing, and a closed position to substantially occlude the internal passageway of the valve housing;
an actuation mechanism slidably mounted to the valve housing in a general linear longitudinal direction and operatively connected to the valve member, the actuation mechanism selectively movable between a first position corresponding to the open position of the valve member and a second position corresponding to the closed position of the valve member; and a lock member supported on the valve housing, the lock member being configured and dimensioned to releasably engage the actuation mechanism to retain the actuation mechanism in either the first position or the second position and wherein the lock member is supported on the valve housing and includes first and second cantilever members, the first cantilever member adapted to releasably secure the actuation mechanism in the first position thereof, the second cantilever member adapted to releasably secure the actuation mechanism in the second position thereof; and a release member mounted with respect to the actuation mechanism and selectively movable relative to the actuation member to cause corresponding movement of one of the first and second cantilever members to cause release of the one of the first and second cantilever members from operative engagement with the actuation mechanism, to thereby permit movement of the actuation mechanism.

10. The valve assembly according to claim 9 wherein the first and second cantilever members are adapted to pivot from a secured condition to an unsecured condition relative to the actuation mechanism upon movement of the release member to thereby permit movement of the actuation mechanism, each cantilever member being normally biased toward the secured condition thereof.

11. A valve assembly for use with a catheter assembly, which comprises:

a valve housing adapted for fluid engagement with a catheter assembly, the valve housing defining a longitudinal axis and having an internal passageway for flow of fluids relative to the catheter assembly;

a valve member at least partially disposed within the valve housing and defining a valve passage, the valve member adapted for movement within the valve housing between an open position wherein the valve passage is in general alignment with the internal passageway of the valve housing to permit flow of fluids through the valve housing, and a closed position to substantially occlude the internal passageway of the valve housing; and an actuation mechanism having a first end and a second end mounted to the valve housing and operatively connected to the valve member, the actuation mechanism being slidably supported on the valve housing in a general linear direction parallel to the longitudinal axis of the valve housing to cause corresponding movement of the valve member between the open position and the closed position;

a lock member supported on the valve housing, the lock member being configured and positioned to releasably retain the valve member in the open and closed positions, wherein the lock member includes at least one flexible member positioned to engage surfaces of the actuation mechanism to retain the valve member in the open position and in the closed position, the at least one flexible member being cantilevered to the valve housing; and the at least one flexible member including first and second flexible members; and further including a release member which is movably supported on the valve housing in relation to the actuation mechanism to a position to disengage the lock member from engagement with the actuation mechanism.

* * * * *